United States Patent [19]

Berg

[11] Patent Number: 4,996,333
[45] Date of Patent: Feb. 26, 1991

[54] CONVERSION OF ACETIC ACID INTO DIKETENE AND WATER USING DIMETHYLSULFOXIDE AND PELARGONIC ACID

[75] Inventor: Lloyd Berg, 1314 S. Third Ave., Bozeman, Mont. 59715

[73] Assignee: Lloyd Berg, Bozeman, Mont.

[21] Appl. No.: 557,601

[22] Filed: Jul. 23, 1990

[51] Int. Cl.$^5$ .......................................... C07D 305/12
[52] U.S. Cl. ..................................... 549/328; 568/302
[58] Field of Search ............... 549/329, 328; 568/301, 568/302

[56] References Cited

U.S. PATENT DOCUMENTS 2,465,337 3/1949 Miller ................................... 549/328
2,513,825 7/1950 Sorenson ............................. 549/328
2,806,064 10/1957 McKlareen ......................... 568/301

OTHER PUBLICATIONS

Stolaiski et al, Chem. Abst., vol. 81, #3269c (1974).

Primary Examiner—James H. Reamer

[57] ABSTRACT

Acetic acid can be almost completely converted into diketene and water by heating it with a mixture of dimethylsulfoxide and pelargonic acid at 120°–150° C. for fifteen to thirty minutes.

1 Claim, No Drawings

CONVERSION OF ACETIC ACID INTO DIKETENE AND WATER USING DIMETHYLSULFOXIDE AND PELARGONIC ACID

FIELD OF THE INVENTION

This invention relates to a process for making diketene from acetic acid using dimethylsulfoxide and pelargonic acid as the agent.

DESCRIPTION OF THE PRIOR ART

Ketene is currently produced by the thermal decomposition of acetic acid or acetone. With acetone, the decomposition temperature is 700° C.; with acetic acid it is 500° C. Ketene is a gas boiling at −41° C. If allowed to dimerize, it will produce diketene, a liquid boiling at 127° C. Commercially, ketene and diketene are made from acetic acid instead of acetone because of the lower temperature required to decompose it.

OBJECTIVE

The object of this invention is to provide a process or method for preparing ketene and diketene from acetic acid at a moderate temperature.

SUMMARY OF THE INVENTION

The object of the invention is provided by a process for making ketene and diketene from acetic acid by heating the acetic acid with a mixture of dimethylsulfoxide and pelargonic acid at a temperature in the range of 120–150° C.

DETAILED DESCRIPTION OF THE INVENTION

I have discovered that when acetic acid is contacted with a mixture of dimethylsulfoxide and pelargonic acid, and heated to 120–150° C., which is the boiling point of the mixture at 1 Atm., the acetic acid will decompose into ketene and water. If the reaction mixture is allowed to boil under a column at total reflux for a quarter to a half hour, most of the ketene will dimerize into diketene. The boiling points of the compounds encountered are:

| Compound | Boiling Point, °C. |
| --- | --- |
| Ketene, $CH_2C=O$ | −41 |
| Water, $H_2O$ | 100 |
| Acetic acid | 118 |
| Diketene, $CH_3-CO-CH=C=O$ | 127 |
| Dimethylsulfoxide, $(CH_3)_2SO$ | 189 |
| Pelargonic acid, $C_8H_{17}COOH$ | 253 |

The ketene dimerizes in the reactor and column. It boils at 127° C. and is condensed and refluxed to the reactor. The acetic acid decomposes as it is converted into ketene and water and since the gaseous ketene is constantly being removed from the mixture, the acetic acid is not recreated from the ketene.

THE USEFULNESS OF THE INVENTION

The usefulness or utility of this invention is that it enables the decomposition of acetic acid into ketene and water at a much lower temperature, 120–150° C., and avoids the thermal decomposition to non-valuable by-products resulting at 500° C. otherwise required. It also enables a high conversion of ketene to diketene if that product is desired.

WORKING EXAMPLE

Forty grams of acetic acid, 25 grams of dimethylsulfoxide and 25 grams of pelargonic acid were heated in the stillpot of a rectification column which had been calibrated with ethyl benzene and m-xylene to possess 7.3 theoretical plates. After one half hour at total reflux, the overhead and stillpot were sampled and analysed by gas chromatograph The overhead composition was 39.7% diketene, 59.6% water and 0.7% acetic acid. The stillpot composition was 11.1% diketene, 12.9% water and 76% acetic acid. These compositions indicate the ease of separation of the diketene from the acetic acid.

I claim:

1. A method for converting acetic acid into diketene which comprises heating acetic acid in a mixture of dimethylsulfoxide and pelargonic acid for about a half hour at a temperature in the range of 120–150° C., distilling the resulting product to recover the diketene and the water as overhead products and recovering the dimethylsulfoxide, pelargonic acid and unconverted acetic acid from the stillpot.

* * * * *